United States Patent
Lang

(12)
(10) Patent No.: US 6,180,663 B1
(45) Date of Patent: Jan. 30, 2001

(54) THERAPEUTIC NASAL INHALANT

(76) Inventor: Stanley Lang, R.R. #4 Box #453, Du Bois, PA (US) 15801

(*) Notice: Under 35 U.S.C. 154(b), the term of this patent shall be extended for 0 days.

(21) Appl. No.: 09/453,632

(22) Filed: Dec. 3, 1999

(51) Int. Cl.[7] .................. A61K 31/375; A61K 31/352; A61K 33/14; A61K 33/00; A61K 35/78
(52) U.S. Cl. ............... 514/474; 514/451; 514/453; 514/456; 514/457; 514/458; 514/464; 514/826; 514/849; 514/853; 514/885; 514/888; 424/663; 424/680; 424/717; 424/195.1; 128/200.14
(58) Field of Search ................ 514/474, 456–458, 514/464, 853, 451, 453, 826, 849, 885, 888; 424/195.1, 717, 663, 680; 128/200.14

(56) References Cited

U.S. PATENT DOCUMENTS 4,940,728 * 7/1990 Postley .......................... 514/474
5,840,278 * 11/1998 Coleman ........................ 424/45

OTHER PUBLICATIONS

Chemical Abstracts 88:27799, 1978.*

* cited by examiner

*Primary Examiner*—John Pak

(57) ABSTRACT

A therapeutic nasal inhalant for using bioflavanoids as a topical antioxidant. The therapeutic nasal inhalant includes a method for making a therapeutic nasal inhalant composition for treating nasal mucosa. The method comprises the steps of mixing together two cups of water, one teaspoon of baking soda, one teaspoon of sodium chloride, and four milligrams of vitamin C to form a mixture. Mixing a bioflavanoid with the mixture. Allowing the mixture to stand. Filtering the mixture. Allowing the mixture to stand for a second time. Filtering the mixture.

3 Claims, No Drawings

THERAPEUTIC NASAL INHALANT

BACKGROUND OF THE INVENTION

1. Field of the Invention

The present invention relates to bioflavanoid compounds and more particularly pertains to a new therapeutic nasal inhalant for using bioflavanoids as a topical antioxidant.

2. Description of the Prior Art

The use of bioflavanoid compounds is known in the prior art. More specifically, bioflavanoid compounds heretofore devised and utilized are known to consist basically of familiar, and expected configurations, notwithstanding the myriad of designs encompassed by the crowded prior art which have been developed for the fulfillment of countless objectives and requirements.

Known prior art includes U.S. Pat. No. 5,653,987; U.S. Pat. No. 5,059,347; U.S. Pat. No. 5,626,883; U.S. Pat. No. 5,747,533; and U.S. Pat. No. 5,817,630.

While these devices fulfill their respective, particular objectives and requirements, the aforementioned patents do not disclose a new therapeutic nasal inhalant. The inventive device includes a method for making a therapeutic nasal inhalant composition for treating nasal mucosa. The method comprises the steps of mixing together two cups of water, one teaspoon of baking soda, one teaspoon of sodium chloride, and four milligrams of vitamin C to form a mixture. Mixing a bioflavanoid with the mixture. Allowing the mixture to stand. Filtering the mixture. Allowing the mixture to stand for a second time. Filtering the mixture.

In these respects, the therapeutic nasal inhalant according to the present invention substantially departs from the conventional concepts and designs of the prior art, and in so doing provides an apparatus primarily developed for the purpose of using bioflavanoids as a topical antioxidant.

SUMMARY OF THE INVENTION

In view of the foregoing disadvantages inherent in the known types of bioflavanoid compounds now present in the prior art, the present invention provides a new therapeutic nasal inhalant construction wherein the same can be utilized for using bioflavanoids as a topical antioxidant.

The general purpose of the present invention, which will be described subsequently in greater detail, is to provide a new therapeutic nasal inhalant apparatus and method which has many of the advantages of the bioflavanoid compounds mentioned heretofore and many novel features that result in a new therapeutic nasal inhalant which is not anticipated, rendered obvious, suggested, or even implied by any of the prior art bioflavanoid compounds, either alone or in any combination thereof.

To attain this, the present invention generally comprises a method for making a therapeutic nasal inhalant composition for treating nasal mucosa. The method comprises the steps of mixing together two cups of water, one teaspoon of baking soda, one teaspoon of sodium chloride, and four milligrams of vitamin C to form a mixture. Mixing a bioflavanoid with the mixture. Allowing the mixture to stand. Filtering the mixture. Allowing the mixture to stand for a second time. Filtering the mixture.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new therapeutic nasal inhalant apparatus and method which has many of the advantages of the bioflavanoid compounds mentioned heretofore and many novel features that result in a new therapeutic nasal inhalant which is not anticipated, rendered obvious, suggested, or even implied by any of the prior art bioflavanoid compounds, either alone or in any combination thereof.

It is another object of the present invention to provide a new therapeutic nasal inhalant which may be easily and efficiently manufactured and marketed.

An even further object of the present invention is to provide a new therapeutic nasal inhalant which is susceptible of a low cost of manufacture with regard to both materials and labor, and which accordingly is then susceptible of low prices of sale to the consuming public, thereby making such therapeutic nasal inhalant economically available to the buying public.

Still yet another object of the present invention is to provide a new therapeutic nasal inhalant which provides in the apparatuses and methods of the prior art some of the advantages thereof, while simultaneously overcoming some of the disadvantages normally associated therewith.

Still another object of the present invention is to provide a new therapeutic nasal inhalant for using bioflavanoids as a topical antioxidant.

Yet another object of the present invention is to provide a new therapeutic nasal inhalant which includes a method for making a therapeutic nasal inhalant composition for treating nasal mucosa. The method comprises the steps of mixing together two cups of water, one teaspoon of baking soda, one teaspoon of sodium chloride, and four milligrams of vitamin C to form a mixture. Mixing a bioflavanoid with the mixture. Allowing the mixture to stand. Filtering the mixture. Allowing the mixture to stand for a second time. Filtering the mixture.

Still yet another object of the present invention is to provide a new therapeutic nasal inhalant that offers relief from the common cold.

Even still another object of the present invention is to provide a new therapeutic nasal inhalant that gives relief from allergy symptoms of the nose.

Yet another object of the present invention is to provide a new therapeutic nasal inhalant that is helpful in recovering from a sinus infection.

Another object of the present invention is to provide a new therapeutic nasal inhalant that is helpful for relieving dry nasal mucosa.

Yet another object of the present invention is to provide a new therapeutic nasal inhalant that is made from all natural chemicals.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying descriptive matter in which there are illustrated preferred embodiments of the invention.

DESCRIPTION OF THE PREFERRED EMBODIMENT

The therapeutic nasal inhalant 10 generally comprises a method for making a therapeutic nasal inhalant composition for treating nasal mucosa. The method comprising the steps of:

1. STEP 1: Mixing together two cups of water, one teaspoon of baking soda, one teaspoon of sodium chloride, four milligrams of vitamin C to form a mixture.

2. STEP 2: Mixing a bioflavanoid with the mixture. Bioflavanoids are anti-oxidants which are found in forms of plant life. The preferred embodiment utilizes proanthocyanidins, which is a class of bioflavanoids. The ideal proanthocyanidins are obtained from grape seed extract. Seven milligrams of grape seed extract are finely ground and mixes with the mixture. Although a range of grape seed extract from two milligrams to fourteen milligrams may be used, seven milligrams is the preferred weight.

3. STEP 3: The mixture is allowed to stand for preferably twenty-four hours.

4. STEP 4: The mixture is then filtered. Ideally the filtering takes place mixture multiple times.

5. STEP 5: The mixture is again allowed to stand for twenty-four hours. The mixture is allowed to stand in order that particles suspended in the mixture settle out.

6. STEP 6: Filtering the mixture again. Filtering removed particles that were entered into the mixture from the grape seed extract. The particles do not need to be removed but they can cause irritation.

7. STEP 7: Packaging the mixture in a nasal inhaler.

8. STEP 8: Squirting the mixture into a nasal cavity.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form. function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of providing a therapeutic nasal inhalant composition for treating nasal mucosa of a person in need of treatment, said method comprising the steps of:

(a) mixing together two cups of water, one teaspoon of baking soda, one teaspoon of sodium chloride, and four milligrams of vitamin C to form a first mixture;

(b) mixing a bioflavonoid with said first mixture to form a second mixture, wherein said bioflavonoid is selected from the group consisting of proanthocyanidin class of bioflavonoids, wherein said proanthocyanidins are obtained from grape seed extract, wherein said mixing step comprises finely grinding seven milligrams of grape seed extract and mixing said grape seed extract with said first mixture;

(c) allowing said second mixture to stand for twenty-four hours;

(d) filtering multiple times the mixture obtained after step (c);

(e) allowing the filtered mixture obtained after step (d) to stand for twenty-four hours;

(f) filtering the mixture obtained after step (e);

(g) packaging the filtered mixture obtained after step (f) in a nasal inhaler; and (h) squirting the mixture in said nasal inhaler into a nasal cavity of a person in need of therapeutic treatment of nasal mucosa.

2. A method of providing a therapeutic nasal inhalant composition for treating nasal mucosa of a person in need of treatment, said method comprising the steps of:

(a) mixing together water, baking soda, sodium chloride, and four milligrams of vitamin C to form a first mixture;

(b) mixing a bioflavonoid with said first mixture to form a second mixture, wherein said bioflavonoid is selected from the group consisting of proanthocyanidin class of bioflavonoids;

(c) allowing said second mixture to stand for twenty-four hours;

(d) filtering multiple times the mixture obtained after step (c);

(e) allowing the filtered mixture obtained after step (d) to stand for twenty-four hours;

(f) filtering the mixture obtained after step (e);

(g) packaging the filtered mixture obtained after step (f) in a nasal inhaler; and (h) squirting the mixture in said nasal inhaler into a nasal cavity of a person in need of therapeutic treatment of nasal mucosa.

3. The method of providing a therapeutic nasal inhalent composition as in claim 2 wherein said proanthocyanidins are obtained from grape seed extract, wherein said mixing step comprises finely grinding seven milligrams of grape seed extract and mixing said grape seed extract with said first mixture.

* * * * *